United States Patent
Oguro et al.

(10) Patent No.: US 9,775,371 B2
(45) Date of Patent: Oct. 3, 2017

(54) DECANOIC ACID DERIVATIVES AND FLAVORING COMPOSITIONS

(71) Applicant: T. HASEGAWA CO., LTD., Tokyo (JP)

(72) Inventors: Daichi Oguro, Kanagawa (JP); Kenji Haraguchi, Kanagawa (JP); Hiroyasu Takaku, Kanagawa (JP)

(73) Assignee: T. HASEGAWA CO., LTD., Tokyo (JP)

( * ) Notice: Subject to any disclaimer, the term of this patent is extended or adjusted under 35 U.S.C. 154(b) by 372 days.

(21) Appl. No.: 14/370,305

(22) PCT Filed: Feb. 6, 2013

(86) PCT No.: PCT/JP2013/052771
§ 371 (c)(1),
(2) Date: Jul. 2, 2014

(87) PCT Pub. No.: WO2013/129051
PCT Pub. Date: Sep. 6, 2013

(65) Prior Publication Data
US 2014/0377434 A1 Dec. 25, 2014

(30) Foreign Application Priority Data
Feb. 27, 2012 (JP) ................. 2012-040042

(51) Int. Cl.
| | | |
|---|---|---|
| A23L 1/22 | (2006.01) |
| A23L 1/226 | (2006.01) |
| A23C 9/152 | (2006.01) |
| A21D 2/14 | (2006.01) |
| A61K 8/37 | (2006.01) |
| A23D 7/005 | (2006.01) |
| A23D 7/01 | (2006.01) |
| A23F 3/16 | (2006.01) |
| A23F 5/24 | (2006.01) |
| A23L 2/56 | (2006.01) |
| A61Q 19/00 | (2006.01) |
| A23G 9/32 | (2006.01) |
| C07C 69/67 | (2006.01) |
| C07C 69/34 | (2006.01) |
| A23F 5/40 | (2006.01) |
| A23F 5/46 | (2006.01) |
| C11B 9/00 | (2006.01) |

(Continued)

(52) U.S. Cl.
CPC ............ *A23L 1/22642* (2013.01); *A21D 2/14* (2013.01); *A23C 9/152* (2013.01); *A23D 7/0056* (2013.01); *A23D 7/013* (2013.01); *A23D 9/007* (2013.01); *A23D 9/013* (2013.01); *A23F 3/163* (2013.01); *A23F 5/243* (2013.01); *A23F 5/405* (2013.01); *A23F 5/465* (2013.01); *A23G 9/32* (2013.01); *A23L 2/56* (2013.01); *A23L 2/66* (2013.01); *A23L 27/206* (2016.08); *A23L 27/2028* (2016.08); *A61K 8/37* (2013.01); *A61Q 19/00* (2013.01); *C07C 69/34* (2013.01); *C07C 69/67* (2013.01); *C11B 9/0019* (2013.01); *A61K 2800/10* (2013.01)

(58) Field of Classification Search
CPC .... A23L 1/22642; A23L 2/66; A23L 27/2028; A23L 27/206; A23L 2/56; A23C 9/152; A21D 2/14; A61K 8/37; A61K 2800/10; A23D 7/0056; A23D 7/013; A23D 9/007; A23D 9/013; A23F 3/163; A23F 2/56; A23F 5/405; A23F 5/465; A61Q 19/00; A23G 9/32; C07C 69/67; C07C 69/34; C11B 9/0019
USPC .................................. 426/534, 650
See application file for complete search history.

(56) References Cited

U.S. PATENT DOCUMENTS 4,826,693 A * 5/1989 Smith .................. A23C 9/1512
426/34

FOREIGN PATENT DOCUMENTS

| EP | 0 410 446 | 7/1990 |
| JP | 3-58953 | 3/1991 |

(Continued)

OTHER PUBLICATIONS

International Search Report dated Apr. 23, 2013 in International (PCT) Application No. PCT/JP2013/052771.

(Continued)

*Primary Examiner* — Leslie Wong
(74) *Attorney, Agent, or Firm* — Wenderoth, Lind & Ponack, L.L.P.

(57) ABSTRACT

This invention relates to alkyl 5-acyloxydecanoate having formula (1) as follows:

[Chemical Formula 1]

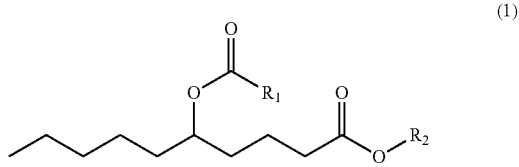

(1)

wherein $R_1$ denotes a hydrogen atom or an alkyl group having one to four carbon atoms, $R_2$ denotes an alkyl group having one to four carbon atoms, with the proviso that the case where $R_1$ is a methyl group and $R_2$ is a methyl group or an ethyl group is excluded, which is capable of giving to food products or the like a characteristic flavor, or a sensory impression, of milk, fat or cream, and to the use of the same in flavoring compositions.

8 Claims, No Drawings

(51) Int. Cl.
*A23D 9/007* (2006.01)
*A23D 9/013* (2006.01)
*A23L 2/66* (2006.01)
*A23L 27/20* (2016.01)

(56) References Cited

FOREIGN PATENT DOCUMENTS

| | | |
|---|---|---|
| JP | 10-168029 | 6/1998 |
| JP | 2003-41287 | 2/2003 |
| JP | 2005-15685 | 1/2005 |
| JP | 2005-143465 | 6/2005 |
| JP | 2005-143466 | 6/2005 |
| JP | 2005-160402 | 6/2005 |
| JP | 2006-20526 | 1/2006 |
| JP | 2006-124490 | 5/2006 |

OTHER PUBLICATIONS

Engel et al., "Biosynthesis of Chiral Flavor and Aroma Compounds in Plants and Microorganisims", American Chemical Society Symposium Series, vol. 388, 1989, pp. 8-22.

Mosandl et al., "Stereoisomeric flavor substances", Z Lebensmittel-Untersuchung und-Forshung, vol. 187 (1), 1988, pp. 40-44.

* cited by examiner

DECANOIC ACID DERIVATIVES AND FLAVORING COMPOSITIONS

TECHNOLOGICAL FIELD

This invention relates to novel decanoic acid derivatives which are useful as a flavoring compound or the like, and to flavoring compositions which comprise said derivative as an effective ingredient.

BACKGROUND ART

Due to diversity in consumer tastes these days, there have been demands for the development of various goods to meet consumers' needs. This tendency is marked especially in the food products trade, and, so, there has been an intense demand for the development of a variety of food products to satisfy consumers' tastes. Also with regard to flavorings which are one of raw materials of food products, flavoring compounds which have been proposed up to now are insufficient to fulfill the needs. Hence, there is an urgent necessity to develop flavoring compounds which are characteristic in the originality and uniqueness of aroma and flavor that are excellent in persistence.

An example of decanoic acid derivative which is known to be a flavoring compound is ethyl 5-hydroxydecanoate, which has been disclosed for use as coffee flavoring (Patent Document 1), fermented milk-like flavoring (Patent Document 2), milk flavoring (Patent Document 3), crustacean flavoring (Patent Document 4), seafood flavoring (Patent Document 5) or seaweed flavoring (Patent Document 6). This compound is, however, unstable, and is hard to be purified by distillation or the like. Methyl 5-acetoxydecanoate which is also known to be a flavoring compound has been disclosed for use as coffee flavoring (Patent Document 1). Although this compound can be purified by distillation, its aroma is not very satisfactory. Ethyl 5-acetoxydecanoate, on the other hand, has been disclosed for use as coffee flavoring (Patent Document 1), crustacean flavoring (Patent Document 4), seafood flavoring (Patent Document 5) or seaweed flavoring (Patent Document 6). This compound, too, can be purified by distillation, but its aroma is not necessarily satisfactory.

CITATION LIST

Patent Literature Documents

Patent Document 1: Japanese Patent Application KOKAI Publication No. 2006-020526
Patent Document 2: Japanese Patent Application KOKAI Publication No. 2006-124490
Patent Document 3: Japanese Patent Application KOKAI Publication No. 2005-015685
Patent Document 4: Japanese Patent Application KOKAI Publication No. 2005-160402
Patent Document 5: Japanese Patent Application KOKAI Publication No. 2005-143466
Patent Document 6: Japanese Patent Application KOKAI Publication No. 2005-143465

SUMMARY OF INVENTION

Technical Problem

The purpose of this invention is to provide a novel compound which is useful as a flavoring to give food products a flavor or a sensory impression of milk, fat or cream, and also to provide a novel flavoring composition which comprises said compound as an effective ingredient.

Solution to Problem

The inventors of this invention have made an assiduous study to solve the above-mentioned problem. As a result, they have synthesized alkyl 5-acyloxydecanoate (except methyl 5-acetoxydecanoate and ethyl 5-acetoxydecanoate) which is a novel decanoic acid derivative, and have found out that the same, when added to a flavoring composition, is capable of giving food products a flavor or a sensory impression of milk, fat or cream. The inventors have thus completed this invention.

This invention provides alkyl 5-acyloxydecanoate having formula (1) as follows:

[Chemical Formula 1]

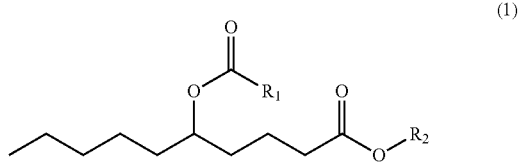

(1)

wherein $R_1$ denotes a hydrogen atom or an alkyl group having one to four carbon atoms, and $R_2$ denotes an alkyl group having one to four carbon atoms, with the proviso that the case where $R_1$ is methyl group and $R_2$ is methyl group or ethyl group is excluded.

This invention also provides a flavoring composition which comprises alkyl 5-acyloxydecanoate of the above-mentioned formula (1) as an effective ingredient.

This invention also provides food products which comprise alkyl 5-acyloxydecanoate of the above-mentioned formula (1).

This invention further provides food products which comprise the above-mentioned flavoring composition.

Advantageous Effects of Invention

Alkyl 5-acyloxydecanoate of this invention is capable of giving to a flavoring composition an original flavor of milk, fat or cream. Furthermore, it is possible to give a flavor of milk, fat or cream to food products or to intensify the characteristic flavor of milk, fat or cream of food products, by adding to the food products a flavoring composition which comprises alkyl 5-acyloxydecanoate of this invention. Thus, a variety of food products to meet consumers' tastes can be provided.

DESCRIPTION OF EMBODIMENTS

In the following, the compounds of the above-mentioned formula (1) and the flavoring composition of this invention are explained in more detail.

In the above-mentioned formula (1), the alkyl group having one to four carbon atoms for which $R_1$ or $R_2$ stand can be straight chain or branched, and concretely includes methyl, ethyl, propyl, isopropyl, butyl, isobutyl, sec-butyl, tert-butyl, etc.

Thus, the alkyl 5-acyloxydecanoate of the above-mentioned formula (1) of this invention include methyl 5-formyloxydecanoate, ethyl 5-formyloxydecanoate, isopropyl 5-formyloxydecanoate, butyl 5-formyloxydecanoate, isopropyl 5-acetyloxydecanoate, butyl 5-acetyloxydecanoate, methyl 5-propionyloxydecanoate, ethyl 5-propionyloxydecanoate, isopropyl 5-propionyloxydecanoate, butyl 5-propionyloxydecanoate, methyl 5-butyryloxydecanoate, ethyl 5-butyryloxydecanoate, isopropyl 5-butyryloxydecanoate, butyl 5-butyryloxydecanoate, ethyl 5-valeryloxydecanoate, etc. For the use as a flavoring compound, methyl 5-formyloxydecanoate and ethyl 5-formyloxydecanoate are preferable, although these two are not exclusive.

Alkyl 5-acyloxydecanoate of the above-mentioned formula (1) of this invention can be produced via a reaction route, for example, as follows:

[Chemical Formula 2]

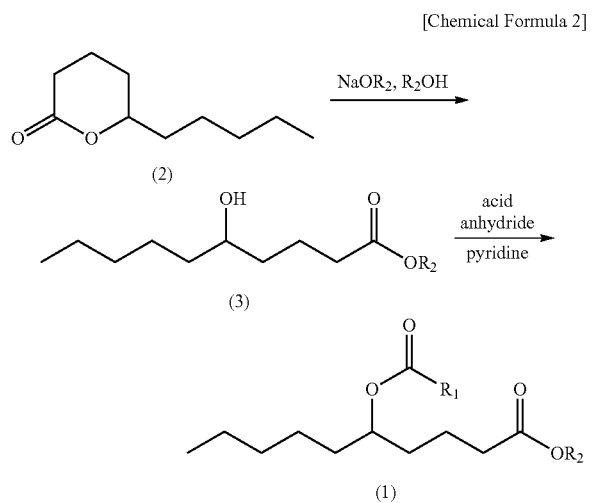

In the above formulae, $R_1$ and $R_2$ are the same as defined above.

Step 1 in the above-mentioned reaction is a transesterification between δ-decalactone and alcohol ($R_2$OH), which can be conducted through usual method, for example by making δ-decalactone of formula (2) react with alcohol either in the presence of metal alkoxide, or in the presence of acid catalyst.

Step 2 in the above-mentioned reaction is an esterification reaction of alkyl 5-hydroxydecanoate of formula (3) as obtained with a derivative of carboxylic acid ($R_1CO_2H$), which can be conducted through usual method, for example by making alkyl 5-hydroxydecanoate of formula (3) react either with carboxylic anhydride (($R_1CO)_2O$), or with carboxylic acid chloride ($R_1COCl$).

In the following, each of the above-mentioned steps is explained with general production method, which however does not restrict this invention.

δ-Decalactone of formula (2) which is used as a starting material for the above-mentioned reaction may be either a product which has been synthesized in accordance with any known method, or a product on the market. Products on the market include δ-decalactone (manufactured by Sigma-Aldrich Co., LLC.), δ-decalactone (manufactured by HighChem Co., Ltd.), etc.

δ-Decalactone of formula (2), when made to react with alcohol ($R_2$OH) in the presence of sodium alkoxide (NaO$R_2$), gives alkyl 5-hydroxydecanoate of formula (3).

Alcohol may be used in a range of normally 1 to 200 moles, preferably 30 to 80 moles, per mole of δ-decalactone. Sodium alkoxide may be used normally in a range of 0.05 to 0.5 mole, preferably 0.1 to 0.3 mole, per mole of δ-decalactone. This reaction may be conducted at temperature normally in a range of 10° C. to 50° C., preferably 15° C. to 40° C., and for normally about 0.5 to about 24 hours, preferably about 0.5 to about 12 hours.

Thus obtained alkyl 5-hydroxydecanoate of formula (3) is subsequently made to react with carboxylic anhydride (($R_1CO)_2O$) or carboxylic acid chloride ($R_1COCl$) in a suitable solvent such as pyridine. Carboxylic anhydride (($R_1CO)_2O$) or carboxylic acid chloride ($R_1COCl$), if added dropwise for example, gives alkyl 5-acyloxydecanoate of formula (1) as desired. Alkyl 5-formyloxydecanoate which is a compound of formula (1) wherein $R_1$ denotes a hydrogen atom and $R_2$ denotes an alkyl group having one to four carbon atoms can be produced by a reaction between alkyl 5-hydroxydecanoate of formula (3) and a mixed acid anhydride of formic acid and another carboxylic acid. Said mixed acid anhydride of formic acid and another carboxylic acid may be prepared by any known method.

Carboxylic anhydride or carboxylic acid chloride may be used in a range of normally 1 to 10 moles, preferably 2 to 5 moles, per mole of alkyl 5-hydroxydecanoate. The reaction between alkyl 5-hydroxydecanoate and carboxylic anhydride or carboxylic acid chloride may be conducted at temperature normally in a range of −5° C. to 50° C., preferably 0° C. to 25° C., and for normally about 30 minutes to about 48 hours, preferably about 1 hour to about 24 hours.

The alkyl 5-acyloxydecanoate of formula (1) of this invention, when added to food products, cosmetics, products for hygienic use or medicines, gives a characteristic flavor of, or a sensory impression of, milk, fat or cream to these products or intensifies the characteristic flavor of milk, fat or cream of these products. The alkyl 5-acyloxydecanoate of formula (1) of this invention may also be mixed with other flavoring components to prepare a milk flavoring composition. Such a milk flavoring composition, when added to food products, cosmetics, products for hygienic use or medicines, gives a characteristic flavor of, or a sensory impression of, milk, fat or cream to these products or intensifies the characteristic flavor of milk, fat or cream of these products. Two or more species of the alkyl 5-acyloxydecanoate of this invention may be combined at any rate to form a mixture. The alkyl 5-acyloxydecanoate of this invention may also be mixed with other flavoring components.

Other flavoring components which said flavoring composition may comprise along with the alkyl 5-acyloxydecanoate of this invention include synthesized flavorings, natural flavorings, natural essential oils, plant extracts, etc., or, for example, those natural essential oils, natural flavorings and synthesized flavorings which are mentioned in the Japan Patent Office: *Collection of Well-known Prior Arts* published Jan. 14, 2000 (Flavorings), Chapter II Flavorings for Food Products, pp. 88-131. In more detail, said other flavoring components may include publicly known flavoring compounds like lactones such as rcaprolactone, γ-heptalactone, γ-octalactone, γ-nonalactone, γ-decalactone, 7-decen-4-olide, 3-methyl-4-decen-4-olide, 3-methyl-5-decen-4-olide, γ-undecalactone, γ-dodecalactone, γ-tridecalactone, γ-tetradecalactone, δ-caprolactone, 2-hexen-5-olide, 2-hepten-5-olide, δ-octalactone, 2-octen-5-olide, 4-methyl-5-octanolide, δ-nonalactone, 2-nonen-5-olide, 4-methyl-5-nonanolide, δ-decalactone, 2-decen-5-olide, 4-methyl-5-decanolide, δ-undecalactone, 2-undecen-5-olide, 4-methyl-5-undecanolide, δ-dodecalactone, 2-dodecen-5-olide, 4-methyl-5-dodecanolide, δ-tridecalactone, 2-tridecen-5- olide, 4-methyl-5-tridecanolide, δ-tetradecalactone, 2-tetradecen-5-olide, 2-pentadecen-5-olide, 2-hexadecen-5-olide, 2-heptadecen-5-olide, 2-octadecen-5-olide, 2-nonadecen-5-olide, 2-eicosen-5-olide and ε-decalactone; fatty acids such as propionic acid, butyric acid, valeric acid, isovaleric acid, caproic acid, trans-2-hexenoic acid, heptanoic acid, caprylic acid, nonanoic acid, 5-hydroxynonanoic acid, capric acid, 2-decenoic acid, 4-decenoic acid, 5-decenoic acid, 6-decenoic acid, 9-decenoic acid, 5-hydroxydecenoic acid, 5-hydroxyundecanoic acid, lauric acid, 5-hydroxydodecanoic acid, myristic acid, pentadecanoic acid, isopentadecanoic acid, palmitic acid, heptadecanoic acid, stearic acid, oleic acid, linoleic acid and linolenic acid; aldehydes such as acetaldehyde, propanal, butanal, 2-butenal, hexanal, octanal, 4-heptenal, 2,4-octadienal, nonanal, 2-nonenal, 2,4-nonadienal, 2,6-nonadienal, decanal, 2,4-decadienal, undecanal, 2,4-undecadienal, dodecanal, benzaldehyde, vanillin, ethyl vanillin, furfural and heliotropine diethyl acetal esters such as ethyl formate, ethyl acetate, butyl acetate, isoamyl acetate, decyl acetate, dodecyl acetate, phenethyl acetate, ethyl lactate, ethyl butyrate, ethyl 2-methylbutyrate, ethyl 3-ethylbutyrate, methyl valerate, methyl caproate, ethyl caproate, methyl heptanoate, ethyl heptanoate, ethyl caprylate, isoamyl caprylate, heptyl caprylate, methyl nonanoate, ethyl nonanoate, methyl caprate, ethyl caprate, ethyl undecanoate, methyl laurate, ethyl laurate, ethyl myristate, ethyl palmitate, methyl salicylate, diethyl succinate, diethyl sebacate, ethyl 5-hydroxyhexanoate, ethyl 5-hydroxydecanoate, ethyl 5-hydroxyundecanoate, propyl 5-hydroxydecanoate, isopropyl 5-hydroxydecanoate, 2-methylpropyl 5-hydroxyoctanoate, ethyl 5-hydroxy-9-methyldecanoate, methyl 5-acetoxydecanoate and ethyl 5-acetoxydecanoate; alcohols such as ethanol, propanol, butanol, pentanol, hexanol, heptanol, octanol, nonanol, decanol, benzyl alcohol, phenylethyl alcohol and furfuryl alcohol; ketones such as 2-heptanone, 2-octanone, 3-octanone, 1-octen-3-one, 2-nonanone, 3-nonanone, 8-nonen-2-one, 2-undecanone, 2-tridecanone, acetoin, 5-hydroxy-4-octanone, diacetyl, 2,3-pentadione, 2,3-hexadione, 2,3-heptadione, acetyl-isovaleryl, p-methoxyacetophenone, benzophenone and maltol; nitrogen-containing compounds such as phenylethyl anthranilate, trimethylamine, indole, skatole, pyridine, isoquinoline, pyrazine and methylpyrazine; sulfur-containing compounds such as methanethiol, isobutylmercaptan, 2,4-dithiapentane, dimethyl sulfide, dimethyl disulfide, dimethyl trisulfide, dimethyl sulfoxide, dimethyl sulfone, methylsulfonylmethane, methyl isothiocyanate, ethyl isothiocyanate, allyl isothiocyanate, 2-methyl-3-butanethiol, methional, ethyl thioacetate, methyl thiobutyrate, 3-butenyl isothiocyanate, 2-methyl thiophene, benzothiazole, sulfurol, methyl acetylthiolactate, methyl propionylthiolactate, methyl butyrylthiolactate, methyl valerylthiolactate, methyl 2-methylbutyrylthiolacate, methyl decylylthiolactate, ethyl acetylthiolactate, ethyl propionylthiolactate, ethyl butyrylthiolactate, ethyl valerylthiolactate and propyl isocaproylthiolactate; lipase hydrolyzate of butterfat; protease hydrolyzate of milk protein; and fraction of milk or of manufactured dairy product prepared from milk, condensed milk, powdered milk, whey, butter, cheese, yogurt or a mixture of the same.

A flavoring composition which comprises alkyl 5-acyloxydecanoate of this invention may contain, where necessary, a solvent such as water and ethanol; or a flavor retention agent such as ethyleneglycol, propyleneglycol, dipropyleneglycol, glycerin, hexylene glycol, benzyl benzoate, triethyl citrate, diethyl phthalate, HERCOLYN®, fatty acid triglyceride and fatty acid diglyceride, which are usually employed for flavoring compositions.

Although alkyl 5-acyloxydecanoate of this invention per se has a characteristic aroma, it forms, as time passes, 6-decalactone which has a strong and sweet aroma like that of cream or nut. Hence, alkyl 5-acyloxydecanoate of this invention can be used as a precursor of 6-decalactone.

As stated above, the alkyl 5-acyloxydecanoate of this invention, either separately or in the form of a flavoring composition which contains the same, is capable of giving rich flavor to various products like food products, cosmetics, products for hygienic use or medicines, or is capable of intensifying the flavor of these products.

The food products which may be given a flavor of milk, fat or cream by a flavoring composition which comprises alkyl 5-acyloxydecanoate of this invention, or food products whose flavor of milk, fat or cream may be intensified by said flavoring composition are not restrictive in particular, and may concretely include carbonated drinks such as cola, fruit juice-containing carbonated drinks and milk-containing carbonated drinks; supplemental nutrition drinks such as fruit juice drinks, vegetable drinks, sport drinks, honey drinks, soybean milk, vitamin supplemental drinks, mineral supplemental drinks, nutrition drinks, health-promoting drinks, lactic fermented milk drinks and milk drinks; tea such as green tea, black tea, oolong tea, herbal tea, milk tea and coffee drinks; alcohol drinks such as choo-high (rice liquor cocktail), other cocktail drinks, low-malt beer, fruit liquor and herbal liquor; dairy products such as butter, cheese, milk and yogurt; desserts such as ice cream, low-fat ice sweets, sherbet, yogurt, pudding, jelly and daily desserts, and mixes for the same; sweets and cakes such as caramel, candy, tablet sweets, cracker, biscuit, cookie, pie, chocolate and snack foods, and mixes like cake mix for the same; and general foods like bread, soup and fast foods.

The cosmetics, products for hygienic use or medicines which may be given a flavor of milk, fat or cream by a flavoring composition which comprises alkyl 5-acyloxydecanoate of this invention, or cosmetics, products for hygienic use or medicines whose flavor of milk, fat or cream may be intensified by said flavoring composition are not restrictive in particular, and may concretely include fragrance products, basic skin-care products, makeup products, hair cosmetic, sunscreen preparations, medicinal cosmetic, hair care products, soap, body soap, bath agent, detergent, fabric softener, bleach, aerosols, deodorant and aromatic, repellents, oral care compositions and external skin care preparations.

The amount of alkyl 5-acyloxydecanoate of this invention to be added to food products, cosmetics, products for hygienic use or medicines may differ depending on the purpose of addition or the species of food products or the like. In the case of food products, the proportion of alkyl 5-acyloxydecanoate of this invention may be normally in a range of 1 ppb to 100 ppm, preferably 10 ppb to 10 ppm, based on the total weight of the food product. In said ranges, remarkable effects are shown to give a flavor of milk, fat or cream to the food products or to intensify the flavor of milk, fat or cream of the food products. Whereas, when the proportion of alkyl 5-acyloxydecanoate exceeds 100 ppm in food product, a fat-like bad smell is undesirably given, which is a characteristic flavor of a single alkyl 5-acyloxydecanoate. When, on the other hand, the proportion of alkyl 5-acyloxydecanoate is less than 1 ppb in food product, the particular effects of this invention to give or intensify flavor are not exhibited.

In the following, this invention is explained in more detail by Examples. The scope of this invention is, however, not to be limited to those Examples.

EXAMPLES

Example 1: Synthesis of methyl 5-hydroxydecanoate

Under a nitrogen atmosphere, a 500 mL four neck flask was fed with δ-decalactone (17.0 g, 0.10 mol; manufactured by Sigma-Aldrich Co., LLC.) and methanol (190.0 g), to which sodium methoxide (28% methanol solution, 3.3 g, 0.017 mol; manufactured by Junsei Chemical Co., Ltd.) was added with stirring at room temperature. The resultant mixture was stirred overnight at room temperature, and, after that, glacial acetic acid (1.0 g, 0.017 mol) was added for the sake of neutralization, and, then, the mixture was subjected to vacuum concentration. To thus obtained residue, a saturated saline solution (100 mL) was added, and the resultant mixture was subjected to extraction with ether (200 mL). Thus obtained ether layer was washed with a saturated aqueous solution of sodium hydrogen carbonate (100 mL) and with a saturated saline solution (100 mL) in order, and was then dried with anhydrous magnesium sulfate, and was subsequently subjected to vacuum concentration. Thus, methyl 5-hydroxydecanoate (18.0 g) was produced as a colorless, oily crude product, with a yield of 89%.

Example 2: Synthesis of methyl 5-formyloxydecanoate

A 100 mL three neck flask was fed with methyl 5-hydroxydecanoate (7.9 g, 0.039 mol) as obtained in Example 1 and pyridine (31.6 g; manufactured by Junsei Chemical Co., Ltd.), to which a liquid mixture of acetic anhydride (10.0 g, 0.098 mol) and 98% formic acid (4.6 g, 0.101 mol; manufactured by Junsei Chemical Co., Ltd.) was added dropwise under ice water cooling with stirring at temperature of 0 to 10° C. for 30 minutes. The resultant mixture was stirred overnight at room temperature, and, after that, methanol (17.6 g, 0.55 mol) was added dropwise under ice water cooling at temperature of 5 to 15° C. for 10 minutes, and the mixture was then stirred at room temperature for 30 minutes. Subsequently, this mixture was poured into a cooled 10% hydrochloric acid (100 mL), and the resultant mixture was subjected to extraction with ether (60 mL, twice). Thus obtained ether layer was washed with a cooled 10% hydrochloric acid (100 mL), a saturated aqueous solution of sodium carbonate (100 mL, twice) and with a saturated saline solution (100 mL) in order, and was then dried with anhydrous magnesium sulfate, and was subsequently subjected to vacuum concentration. Thus obtained residue (8.8 g) was purified by distillation to give methyl 5-formyloxydecanoate (the product 1 of this invention; 7.4 g, 0.032 mol) as a colorless, oily matter. Yield from δ-decalactone was 74%.

Gas chromatography of the methyl 5-formyloxydecanoate as obtained in the above Example 2 showed that the same had a chemical purity of 91.4% (Conditions for gas chromatography—Column: TC-1 (30 m×0.53 mm); Temperature Elevation: 100° C.-300° C., an elevation of 20.0° C./min.; Carrier Gas: Nitrogen; Linear Gas Velocity: 60 cm/sec.; Retention Time: 5.8 min.).

Data of Physical Properties of Methyl 5-formyloxydecanoate $^1$H-NMR (400 MHz, CDCl$_3$): δ ppm 0.86 (t, 3H, J=7.0 Hz), 1.20-1.35 (m, 7H), 1.45-1.75 (m, 5H), 2.30 (t, 2H, J=7.0 Hz), 3.65 (s, 3H), 4.98 (quin, 1H, J=6.0 Hz), 8.07 (s, 1H)

$^{13}$C-NMR (100 MHz, CDCl$_3$): δ ppm 13.94, 20.62, 22.48, 24.84, 31.57, 33.32, 33.66, 33.89, 51.54, 73.81, 160.94, 173.68

MS (m/z): 201 (1), 185 (1), 169 (14), 152 (23), 128 (14), 110 (34), 99 (79), 84 (26), 74 (100), 55 (70), 43 (47), 41 (47), 29 (23)

Referential Example 1: Synthesis of Methyl 5-acetoxydecanoate

A 100 mL three neck flask was fed with methyl 5-hydroxydecanoate (10.1 g, 0.05 mol) as obtained in Example 1 and pyridine (40.3 g; manufactured by Junsei Chemical Co., Ltd.), to which acetic anhydride (10.2 g, 0.10 mol) was added dropwise under ice water cooling with stirring at temperature of 5 to 8° C. for 10 minutes. The resultant mixture was stirred overnight at room temperature, and, after that, methanol (18.0 g, 0.56 mol) was added dropwise under ice water cooling at temperature of 5 to 15° C. for 10 minutes, and the mixture was then stirred at room temperature for 30 minutes. Subsequently, this mixture was poured into a cooled 10% hydrochloric acid (100 mL), and the resultant mixture was subjected to extraction with ether (60 mL, twice). Thus obtained ether layer was washed with a cooled 10% hydrochloric acid (100 mL), a saturated aqueous solution of sodium carbonate (100 mL, twice) and with a saturated saline solution (100 mL) in order, and was then dried with anhydrous magnesium sulfate, and was subsequently subjected to vacuum concentration. Thus obtained residue (12.0 g) was purified by distillation to give methyl 5-acetoxydecanoate (the referential product 1; 10.2 g, 0.042 mol) as a colorless, oily matter. Yield from δ-decalactone was 75%.

Gas chromatography of the methyl 5-acetoxydecanoate as obtained in the above Referential Example 1 showed that the same had a chemical purity of 95.6% (Conditions for gas chromatography were the same as in Example 2; Retention Time: 6.1 min.).

Example 3: Synthesis of Ethyl 5-hydroxydecanoate

Under a nitrogen atmosphere, a 500 mL four neck flask was fed with δ-decalactone (17.0 g, 0.10 mol; manufactured by Sigma-Aldrich Co., LLC.) and 99% ethanol (270.0 g), to which sodium ethoxide (21% ethanol solution, 5.5 g, 0.017 mol; manufactured by Sigma-Aldrich Co., LLC.) was added with stirring at room temperature. The resultant mixture was stirred overnight at room temperature, and, after that, glacial acetic acid (1.0 g, 0.017 mol) was added for the sake of neutralization, and, then, the mixture was subjected to vacuum concentration. To thus obtained residue, a saturated saline solution (100 mL) was added, and the resultant mixture was subjected to extraction with ether (200 mL). Thus obtained ether layer was washed with a saturated aqueous solution of sodium hydrogen carbonate (100 mL) and with a saturated saline solution (100 mL) in order, and was then dried with anhydrous magnesium sulfate, and was subsequently subjected to vacuum concentration. Thus, ethyl 5-hydroxydecanoate (18.4 g) was produced as a colorless, oily crude product, with a yield of 85%.

Example 4: Synthesis of Ethyl 5-formyloxydecanoate

A 100 mL three neck flask was fed with ethyl 5-hydroxydecanoate (7.6 g, 0.035 mol) as obtained in Example 3 and pyridine (30.4 g; manufactured by Junsei Chemical Co., Ltd.), to which a liquid mixture of acetic anhydride (9.0 g, 0.088 mol) and 98% formic acid (4.2 g, 0.091 mol; manufactured by Junsei Chemical Co., Ltd.) was added dropwise under ice water cooling with stirring at temperature of 0 to 10° C. for 30 minutes. The resultant mixture was stirred overnight at room temperature, and, after that, 99% ethanol (22.6 g, 0.49 mol) was added dropwise under ice water cooling at temperature of 5 to 15° C. for 10 minutes, and the mixture was then stirred at room temperature for 30 minutes. Subsequently, this mixture was poured into a cooled 10% hydrochloric acid (100 mL), and the resultant mixture was subjected to extraction with ether (60 mL, twice). Thus obtained ether layer was washed with a cooled 10% hydrochloric acid (100 mL), a saturated aqueous solution of sodium carbonate (100 mL, twice) and with a saturated saline solution (100 mL) in order, and was then dried with anhydrous magnesium sulfate, and was subsequently subjected to vacuum concentration. Thus obtained residue (8.4 g) was purified by distillation to give ethyl 5-formyloxydecanoate (the product 2 of this invention; 7.0 g, 0.028 mol) as a colorless, oily matter. Yield from δ-decalactone was 69%.

Gas chromatography of the ethyl 5-formyloxydecanoate as obtained in the above Example 4 showed that the same had a chemical purity of 92.1% (Conditions for gas chromatography were the same as in Example 2; Retention Time: 6.3 min.).

Data of Physical Properties of Ethyl 5-formyloxydecanoate
$^1$H-NMR (400 MHz, CDCl$_3$): δ ppm 0.86 (t, 3H, J=7.0 Hz), 1.23 (t, 3H, J=7.0 Hz), 1.20-1.35 (m, 7H), 1.45-1.75 (m, 5H), 2.29 (t, 2H, J=7.0 Hz), 4.11 (q, 2H, J=7.0 Hz), 4.98 (quin, 1H, J=6.0 Hz), 8.07 (s, 1H) $^{13}$C-NMR (100 MHz, CDCl$_3$): δ ppm 13.95, 14.23, 20.63, 22.49, 24.85, 31.57, 33.31, 33.88, 33.93, 60.32, 73.86, 160.95, 173.25 MS (m/z): 215 (1), 199 (2), 169 (20), 152 (36), 135 (12), 128 (12), 110 (53), 99 (88), 88 (100), 69 (42), 55 (84), 41 (58), 29 (48)

Referential Example 2: Synthesis of Ethyl 5-acetoxydecanoate

A 100 mL three neck flask was fed with ethyl 5-hydroxydecanoate (10.1 g, 0.05 mol) as obtained in Example 3 and pyridine (40.3 g; manufactured by Junsei Chemical Co., Ltd.), to which acetic anhydride (10.2 g, 0.10 mol) was added dropwise under ice water cooling with stirring at temperature of 5 to 8° C. for 10 minutes. The resultant mixture was stirred overnight at room temperature, and, after that, methanol (18.0 g, 0.56 mol) was added dropwise under ice water cooling at temperature of 5 to 15° C. for 10 minutes, and the mixture was then stirred at room temperature for 30 minutes. Subsequently, this mixture was poured into a cooled 10% hydrochloric acid (100 mL), and the resultant mixture was subjected to extraction with ether (60 mL, twice). Thus obtained ether layer was washed with a cooled 10% hydrochloric acid (100 mL), a saturated aqueous solution of sodium carbonate (100 mL, twice) and with a saturated saline solution (100 mL) in order, and was then dried with anhydrous magnesium sulfate, and was subsequently subjected to vacuum concentration. Thus obtained residue (12.7 g) was purified by distillation to give ethyl 5-acetoxydecanoate (the referential product 2; 10.1 g, 0.039 mol) as a colorless, oily matter. Yield from δ-decalactone was 67%.

Gas chromatography of the ethyl 5-acetoxydecanoate as obtained in the above Referential Example 2 showed that the same had a chemical purity of 96.9% (Conditions for gas chromatography were the same as in Example 2; Retention Time: 6.5 min.).

Example 5: Evaluation of Aroma

Well-trained five panelists evaluated the aroma of 0.1% ethanol solution of each of methyl 5-formyloxydecanoate (the product 1 of this invention), ethyl 5-formyloxydecanoate (the product 2 of this invention), methyl 5-acetoxydecanoate (the referential product 1) and ethyl 5-acetoxydecanoate (the referential product 2). For this evaluation of aroma, the above-mentioned 0.1% ethanol solution was prepared in a 30 mL sample bottle, and the panelists smelled the mouth of the bottle and a piece of paper permeated with the solution. Average evaluation of aroma by the five panelists is shown in Table 1.

[Table 1]

TABLE 1

| Evaluation of aroma | |
|---|---|
| Compound | Evaluation of aroma |
| Methyl 5-formyloxydecanoate (the product 1 of this invention) | Characteristic sensory impression of cream or milk, or mealy or soapy impression of fat |
| Ethyl 5-formyloxydecanoate (the product 2 of this invention) | Characteristic sensory impression of cream or milk, or butter-like impression of fat |
| Methyl 5-acetoxydecanoate (the referential product 1) | Sensory impression of cream or milk, or wax-like impression of cheese |
| Ethyl 5-acetoxydecanoate (the referential product 2) | Sensory impression of cream or milk, or wax-like or soapy impression of fat |

Example 6: Effects of Addition to a Milk-Like Formulated Flavoring Composition

Milk-like formulated flavoring composition was prepared from the components (mass %) as shown in Table 2 below. With said milk-like formulated flavoring composition (comparative product 1), 2.0 g of the product 1 or 2 of this invention was mixed to give novel milk-like formulated flavoring compositions, i.e., the products 3 and 4 of this invention. These products 3 and 4 of this invention as well as comparative product 1 were subjected to organoleptic evaluation by well-trained 10 panelists.

TABLE 2

| Formulation of milk-like formulated flavoring compositions | | | |
|---|---|---|---|
| | Comparative product 1 | Product 3 of this invention | Product 4 of this invention |
| Vanillin | 25.0 | 25.0 | 25.0 |
| Ethyl vanillin | 35.0 | 35.0 | 35.0 |
| Cyclotene | 2.5 | 2.5 | 2.5 |
| Ethyl maltol | 3.5 | 3.5 | 3.5 |
| γ-Nonalactone | 10.0 | 10.0 | 10.0 |
| γ-Decalactone | 2.5 | 2.5 | 2.5 |
| δ-Decalactone | 2.5 | 2.5 | 2.5 |
| γ-Undecalactone | 2.0 | 2.0 | 2.0 |
| Acetyl methyl carbinol | 3.0 | 3.0 | 3.0 |
| Diacetyl | 7.0 | 7.0 | 7.0 |
| Butyric acid | 5.0 | 5.0 | 5.0 |
| Propyleneglycol | 902.0 | 900.0 | 900.0 |
| Product 1 of this invention | — | 2.0 | — |
| Product 2 of this invention | — | — | 2.0 |
| Total | 1000.0 | 1000.0 | 1000.0 |

As a result, all the ten panelists said that the products 3 and 4 of this invention distinctively gave a favorable sensory impression of milk and were creamy, as compared with comparative product 1.

Example 7: Effects of Addition to a Butter-Like Formulated Flavoring Composition Butter-like formulated flavoring composition was prepared from the components (mass %) as shown in Table 3 below. With said butter-like formulated flavoring composition (comparative product 2), 5.0 g of the product 1 or 2 of this invention was mixed to give novel butter-like formulated flavoring compositions, i.e., the products 5 and 6 of this invention. These products 5 and 6 of this invention as well as comparative product 2 were subjected to organoleptic evaluation by well-trained 10 panelists.

TABLE 3

Formulation of butter-like formulated flavoring compositions

|  | Comparative product 2 | Product 5 of this invention | Product 6 of this invention |
|---|---|---|---|
| Methyl undecyl ketone | 2.0 | 2.0 | 2.0 |
| δ-Decalactone | 27.0 | 27.0 | 27.0 |
| δ-Dodecalactone | 58.0 | 58.0 | 58.0 |
| Butyric acid | 4.0 | 4.0 | 4.0 |
| Methyl heptyl ketone | 0.4 | 0.4 | 0.4 |
| γ-Decalactone | 0.6 | 0.6 | 0.6 |
| Acetyl methyl carbitol | 8.0 | 8.0 | 8.0 |
| Vegetable oil | 400.0 | 395.0 | 395.0 |
| Product 1 of this invention | — | 5.0 | — |
| Product 2 of this invention | — | — | 5.0 |
| Total | 500.0 | 500.0 | 500.0 |

As a result, all the ten panelists said that the products 5 and 6 of this invention distinctively gave a favorable sensory impression of butter and also a rich flavor characteristic of butterfat, as compared with comparative product 2.

Example 8: Effects of the Addition of Product 1 of this Invention to Milk Coffee Milk coffee (control product 1) was prepared in accordance with the formulation (weight %) as shown in Table 4 below.

TABLE 4

Formulation of milk coffee

|  | (g) |
|---|---|
| Coffee extract Bx. 2.7 | 500.0 |
| Castor sugar | 60.0 |
| Whole milk powder | 5.0 |
| Powdered skim milk | 5.0 |
| Sucrose ester HLB 15 | 0.5 |
| pH Adjuster (Sodium bicarbonate) | 0.9 |
| Coffee flavoring | 1.0 |
| Water | 427.6 |
| Total | 1000.0 |

The product 1 of methyl 5-formyloxydecanoate of this invention was diluted with ethanol and further with water to give a 1% solution. Milk coffee (control product 1) was mixed with 10 μg of said 1% solution (to give comparative product 3 in which the concentration of the product 1 of this invention was 0.1 ppb); with 100 μg of the 1% solution (to give the product 7 of this invention in which the concentration of the product 1 of this invention was 1 ppb); with 1 mg of the 1% solution (to give the product 8 of this invention in which the concentration of the product 1 of this invention was 10 ppb); with 10 mg of the 1% solution (to give the product 9 of this invention in which the concentration of the product 1 of this invention was 100 ppb); with 100 mg of the 1% solution (to give the product 10 of this invention in which the concentration of the product 1 of this invention was 1 ppm); with 1 g of the 1% solution (to give the product 11 of this invention in which the concentration of the product 1 of this invention was 10 ppm); with 10 g of the 1% solution (to give the product 12 of this invention in which the concentration of the product 1 of this invention was 100 ppm); and with 100 g of the 1% solution (to give comparative product 4 in which the concentration of the product 1 of this invention was 1000 ppm). These products of milk coffee were subjected to flavor evaluation by well-trained 10 panelists. Results of comparison with control product 1 to which the product 1 of this invention had not been added are shown in Table 5 below.

TABLE 5

Evaluation of flavor of milk coffee

|  | Concentration of product 1 of this invention in the milk coffee | Evaluation of flavor |
|---|---|---|
| Comparative product 3 | 0.1 ppb | Much the same as the control product |
| Product 7 of this invention | 1 ppb | A milk-like aroma intensified, with a slight creamy body, as compared with the control product |
| Product 8 of this invention | 10 ppb | A favorable milk-like aroma intensified, with a creamy body, as compared with the control product |
| Product 9 of this invention | 100 ppb | A favorable milk-like aroma markedly intensified, with a rich and good creamy body, as compared with the control product |
| Product 10 of this invention | 1 ppm | A favorable milk-like aroma markedly intensified, with a rich and good creamy body, as compared with the control product |
| Product 11 of this invention | 10 ppm | A milk-like aroma markedly intensified, with a slightly heavyweight creamy body, as compared with the control product |
| Product 12 of this invention | 100 ppm | A milk-like aroma markedly intensified, with a heavyweight creamy body, as compared with the control product |
| Comparative product 4 | 1000 ppm | Too strong sensory impression of milk, with the native aroma of milk coffee lost |

As is seen from the evaluation results of Table 5, the products 7-12 of this invention had an intensified milk aroma with a creamy body. The products 9 and 10 of this invention, in particular, had a markedly intensified favorable milk-like aroma, with a rich and good creamy body. On the other hand, comparative product 3 was much the same as the control product 1, and comparative product 4 had lost the native aroma of milk coffee.

Example 9: Effects of the Addition of Product 2 of this Invention to Milk Coffee The product 2 of ethyl 5-formyloxydecanoate of this invention was diluted with ethanol and further with water to give a 1% solution of ethyl 5-formyloxydecanoate. Milk coffee (control product 1) was mixed with 10 μg of said 1% solution to give comparative product 5 (in which the concentration of the product 2 of this invention was 0.1 ppb); with 100 μg of the 1% solution to give the product 13 of this invention (in which the concentration of the product 2 of this invention was 1 ppb); with 1 mg of the 1% solution to give the product 14 of this invention (in which the concentration of the product 2 of this invention was 10 ppb); with 10 mg of the 1% solution to give the product 15 of this invention (in which the concentration of the product 2 of this invention was 100 ppb); with 100 mg of the 1% solution to give the product 16 of this invention (in which the concentration of the product 2 of this invention was 1 ppm): with 1 g of the 1% solution to give the product 17 of this invention (in which the concentration of the product 2 of this invention was 10 ppm): with 10 g of the 1% solution to give the product 18 of this invention (in which the concentration of the product 2 of this invention was 100 ppm): and with 100 g of the 1% solution to give comparative product 6 (in which the concentration of the product 2 of this invention was 1000 ppm). These products of milk coffee were subjected to flavor evaluation by well-trained 10 panelists. Results of comparison with control product 1 to which the product 2 of this invention had not been added are shown in Table 6 below.

TABLE 6

Evaluation of flavor of milk coffee

| | Concentration of product 2 of this invention in the milk coffee | Evaluation of flavor |
|---|---|---|
| Comparative product 5 | 0.1 ppb | Much the same as the control product |
| Product 13 of this invention | 1 ppb | A milk-like aroma intensified, with a slight creamy body, as compared with the control product |
| Product 14 of this invention | 10 ppb | A favorable milk-like aroma intensified, with a creamy body, as compared with the control product |
| Product 15 of this invention | 100 ppb | A favorable milk-like aroma markedly intensified, with a rich and good creamy body, as compared with the control product |
| Product 16 of this invention | 1 ppm | A favorable milk-like aroma markedly intensified, with a rich and good creamy body, as compared with the control product |
| Product 17 of this invention | 10 ppm | A milk-like aroma markedly intensified, with a slightly heavyweight creamy body, as compared with the control product |
| Product 18 of this invention | 100 ppm | A milk-like aroma markedly intensified, with a heavyweight creamy body, as compared with the control product |
| Comparative product 6 | 1000 ppm | Too strong sensory impression of milk, with the native aroma of milk coffee lost |

As is seen from the evaluation results of Table 6, the products 13-18 of this invention had an intensified milk aroma with a creamy body. The products 15 and 16 of this invention, in particular, had a markedly intensified favorable milk-like aroma, with a rich and good creamy body. On the other hand, comparative product 5 was much the same as the control product 1, and comparative product 6 had lost the native aroma of milk coffee.

Example 10: Effects of the Addition of Product 1 of this Invention to Ice Cream

Ice cream (control product 2) was prepared in accordance with the formulation (weight %) as shown in Table 7 below.

TABLE 7

Formulation of ice cream

| | (g) |
|---|---|
| Milk | 500 |
| 40% Fresh cream | 160 |
| Powdered skim milk | 40 |
| Sugar | 100 |
| 70% Saccharified starch syrup | 80 |
| Emulsion stabilizer | 5 |
| Water | 115 |
| Total | 1000 |

The product 1 of methyl 5-formyloxydecanoate of this invention was diluted with ethanol and further with water to give a 1% solution of methyl 5-formyloxydecanoate. Ice cream (control product 2) was mixed with 10 μg of said 1% solution to give comparative product 7 (in which the concentration of the product 1 of this invention was 0.1 ppb); with 100 μg of the 1% solution to give the product 19 of this invention (in which the concentration of the product 1 of this invention was 1 ppb); with 1 mg of the 1% solution to give the product 20 of this invention (in which the concentration of the product 1 of this invention was 10 ppb); with 10 mg of the 1% solution to give the product 21 of this invention (in which the concentration of the product 1 of this invention was 100 ppb); with 100 mg of the 1% solution to give the product 22 of this invention (in which the concentration of the product 1 of this invention was 1 ppm); with 1 g of the 1% solution to give the product 23 of this invention (in which the concentration of the product 1 of this invention was 10 ppm); with 10 g of the 1% solution to give the product 24 of this invention (in which the concentration of the product 1 of this invention was 100 ppm); and with 100 g of the 1% solution to give comparative product 8 (in which the concentration of the product 1 of this invention was 1000 ppm). These products of ice cream were subjected to flavor evaluation by well-trained 10 panelists. Results of comparison with control product 2 to which the product 1 of this invention had not been added are shown in Table 8 below.

TABLE 8

Evaluation of flavor of ice cream

| | Concentration of product 1 of this invention in the milk coffee | Evaluation of flavor |
|---|---|---|
| Comparative product 7 | 0.1 ppb | Much the same as the control product |
| Product 19 of this invention | 1 ppb | A milk-like aroma intensified, with a slight sensory impression of butterfat, as compared with the control product |
| Product 20 of this invention | 10 ppb | A favorable milk-like aroma intensified, with a sensory impression of butterfat, as compared with the control product |
| Product 21 of this invention | 100 ppb | A favorable milk-like aroma markedly intensified, with a refreshing impression of butterfat, as compared with the control product |
| Product 22 of this invention | 1 ppm | A favorable milk-like aroma markedly intensified, with a refreshing impression of butterfat, as compared with the control product |
| Product 23 of this invention | 10 ppm | A milk-like aroma markedly intensified, with a slightly heavyweight impression of butterfat, as compared with the control product |

TABLE 8-continued

Evaluation of flavor of ice cream

| | Concentration of product 1 of this invention in the milk coffee | Evaluation of flavor |
|---|---|---|
| Product 24 of this invention | 100 ppm | A milk-like aroma markedly intensified, with a heavyweight impression of butterfat, as compared with the control product |
| Comparative product 8 | 1000 ppm | Too strong sensory impression of milk, with a bad smell different from the native aroma of ice cream |

As is seen from the evaluation results of Table 8, the products 19-24 of this invention had an intensified milk aroma with a sensory impression of butterfat. The products 21 and 22 of this invention, in particular, had a markedly intensified favorable milk-like aroma, with a refreshing impression of butterfat. On the other hand, comparative product 7 was much the same as the control product 2, and comparative product 8 had a bad smell different from the native aroma of ice cream.

Example 11: Effects of the Addition of Product 2 of this Invention to Ice Cream The product 2 of ethyl 5-formyloxydecanoate of this invention was diluted with ethanol and further with water to give a 1% solution of ethyl 5-formyloxydecanoate. Ice cream (control product 2) was mixed with 10 μg of said 1% solution of ethyl 5-formyloxydecanoate to give comparative product 9 (in which the concentration of the product 2 of this invention was 0.1 ppb); with 100 μg of the 1% solution to give the product 25 of this invention (in which the concentration of the product 2 of this invention was 1 ppb); with 1 mg of the 1% solution to give the product 26 of this invention (in which the concentration of the product 2 of this invention was 10 ppb); with 10 mg of the 1% solution to give the product 27 of this invention (in which the concentration of the product 2 of this invention was 100 ppb); with 100 mg of the 1% solution to give the product 28 of this invention (in which the concentration of the product 2 of this invention was 1 ppm): with 1 g of the 1% solution to give the product 29 of this invention (in which the concentration of the product 2 of this invention was 10 ppm): with 10 g of the 1% solution to give the product 30 of this invention (in which the concentration of the product 2 of this invention was 100 ppm): and with 100 g of the 1% solution to give comparative product 10 (in which the concentration of the product 2 of this invention was 1000 ppm). These products of ice cream were subjected to flavor evaluation by well-trained 10 panelists. Results of comparison with control product 2 to which the product 2 of this invention had not been added are shown in Table 9 below.

TABLE 9

Evaluation of flavor of ice cream

| | Concentration of product 2 of this invention in the milk coffee | Evaluation of flavor |
|---|---|---|
| Comparative product 9 | 0.1 ppb | Much the same as the control product |
| Product 25 of this invention | 1 ppb | A milk-like aroma intensified, with a slight sensory impression of butterfat, as compared with the control product |
| Product 26 of this invention | 10 ppb | A favorable milk-like aroma intensified, with a sensory impression of butterfat, as compared with the control product |
| Product 27 of this invention | 100 ppb | A favorable milk-like aroma markedly intensified, with a refreshing impression of butterfat, as compared with the control product |
| Product 28 of this invention | 1 ppm | A favorable milk-like aroma markedly intensified, with a refreshing impression of butterfat, as compared with the control product |
| Product 29 of this invention | 10 ppm | A milk-like aroma markedly intensified, with a slightly heavyweight impression of butterfat, as compared with the control product |
| Product 30 of this invention | 100 ppm | A milk-like aroma markedly intensified, with a heavyweight impression of butterfat, as compared with the control product |
| Comparative product 10 | 1000 ppm | Too strong sensory impression of milk, with a bad smell different from the native aroma of ice cream |

As is seen from the evaluation results of Table 9, the products 25-30 of this invention had an intensified milk aroma with a sensory impression of butterfat. The products 27 and 28 of this invention, in particular, had a markedly intensified favorable milk-like aroma, with a refreshing impression of butterfat. On the other hand, comparative product 9 was much the same as the control product 2, and comparative product 10 had a bad smell different from the native aroma of ice cream.

Example 12: Effects of Addition of a Milk-Like Formulated Flavoring Composition to Milk Tea Milk-like formulated flavoring compositions as obtained in Example 6 (comparative product 1, and the products 3 and 4 of this invention) were added to milk tea which had been prepared in accordance with the formulation as shown in Table 10 below, by which to produce, by a normal method, milk tea drinks of comparative product 11, and the products 31 and 32 of this invention, respectively. These products of milk tea were subjected to organoleptic evaluation by well-trained 20 panelists.

TABLE 10

Formulation of milk tea

| | Comparative product 11, | Product 31 of this invention | Product 32 of this invention |
|---|---|---|---|
| Black tea extract | 420 | 420 | 420 |
| Castor sugar | 120 | 120 | 120 |
| Milk | 230 | 230 | 230 |
| Whole milk powder | 20 | 20 | 20 |
| Powdered skim milk | 10 | 10 | 10 |
| Sucrose ester HLB 15 | 1 | 1 | 1 |
| Water | 198 | 198 | 198 |

TABLE 10-continued

| Formulation of milk tea | | | |
|---|---|---|---|
| | Comparative product 11, | Product 31 of this invention | Product 32 of this invention |
| Comparative product 1 | 1 | 0 | 0 |
| Product 3 of this invention | 0 | 1 | 0 |
| Product 4 of this invention | 0 | 0 | 1 |
| Total (g) | 1000 | 1000 | 1000 |

As a result, all the 20 panelists said that the products 31 and 32 of this invention gave a favorable sensory impression of butterfat with a good body, as compared with comparative product 11.

Example 13: Effects of Addition of a Butter-Like Formulated Flavoring Composition to Cookie Butter-like formulated flavoring compositions as obtained in Example 7 (comparative product 2, and the products 5 and 6 of this invention) were added to cookie dough which had been prepared in accordance with the formulation as shown in Table 11 below. Then, the cookie dough was baked at 220° C. for seven minutes to make cookies of comparative product 12, and the products 33 and 34 of this invention, respectively. These cookies were subjected to organoleptic evaluation by well-trained 20 panelists.

TABLE 11

| Formulation of cookie | | | |
|---|---|---|---|
| | Comparative product 12 | Product 33 of this invention | Product 34 of this invention |
| Flour (weak flour) | 500 | 500 | 500 |
| Sugar | 200 | 200 | 200 |
| Shortening (MP 37° C.) | 150 | 150 | 150 |
| Sweetened Condensed Whole Milk | 50 | 50 | 50 |
| Whole milk powder | 20 | 20 | 20 |
| Salt | 5 | 5 | 5 |
| Sodium bicarbonate | 4 | 4 | 4 |
| Ammonium bicarbonate | 5 | 5 | 5 |
| Water | 65 | 65 | 65 |
| Comparative product 2 | 1 | 0 | 0 |
| Product 5 of this invention | 0 | 1 | 0 |
| Product 6 of this invention | 0 | 0 | 1 |
| Total (g) | 1000 | 1000 | 1000 |

As a result, all the 20 panelists said that the products 33 and 34 of this invention gave a sensory impression of characteristic creamy butterfat with a distinctively rich flavor of butter, as compared with comparative product 12.

The invention claimed is:

1. An alkyl 5-acyloxydecanoate of formula (1) as follows:

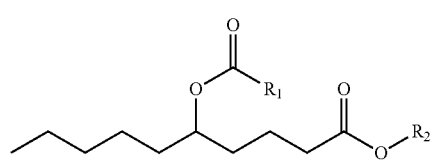

(1)

wherein:
R$_1$ is a hydrogen atom or an alkyl group having one to four carbon atoms, and
R$_2$ is an alkyl group having one to four carbon atoms, with the proviso that the following compounds are excluded:

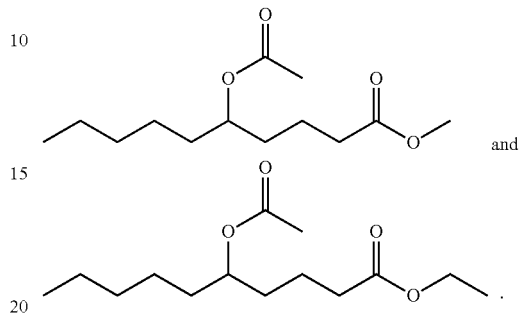

and

2. The compound of claim 1, which is selected from the group consisting of methyl 5-formyloxydecanoate and ethyl 5-formyloxydecanoate.

3. A flavoring composition, which comprises, as an effective ingredient, an alkyl 5-acyloxydecanoate of formula (1) as follows:

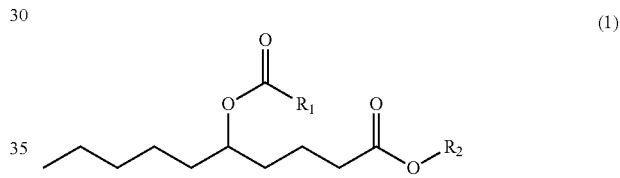

(1)

wherein:
R$_1$ is a hydrogen atom or an alkyl group having one to four carbon atoms, and
R$_2$ is an alkyl group having one to four carbon atoms, with the proviso that the following compounds are excluded:

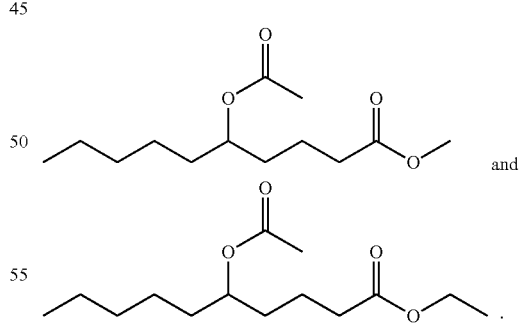

and

4. A food product comprising 1 ppb to 100 ppm of the compound of claim 1.

5. A food product comprising the flavoring composition of claim wherein the flavoring composition comprises 1 ppb to 100 ppm of the compound of formula (1).

6. A food product comprising 1 ppb to 100 ppm of the compound of claim 2.

7. A method of flavoring, comprising combining 1 ppb to 100 ppm of the compound of claim 1 with a food.

8. A method of flavoring, comprising combining the flavoring composition of claim 3 with a food, wherein the flavoring composition comprises 1 ppb to 100 ppm of the compound of formula (1).

* * * * *